United States Patent [19]

Oxford et al.

[11] Patent Number: 4,870,096
[45] Date of Patent: Sep. 26, 1989

[54] 5-SUBSTITUTED 3-ANINOALKYL INDOLES

[75] Inventors: Alexander W. Oxford, Royston; Ian H. Coates, Hertford; David E. Bays, Ware; Colin F. Webb, Royston, all of England

[73] Assignee: Glaxo Group Limited, London, England

[21] Appl. No.: 940,652

[22] Filed: Dec. 11, 1986

[30] Foreign Application Priority Data

Dec. 11, 1985 [GB] United Kingdom ............... 8530507

[51] Int. Cl.$^4$ ................. C07D 209/16; A61K 31/40; A61K 209/18; A61K 209/20
[52] U.S. Cl. .................................. 514/415; 548/503; 548/504; 548/505; 548/507; 564/163; 564/164; 562/433; 562/442
[58] Field of Search ......................... 548/504; 514/415

[56] References Cited

U.S. PATENT DOCUMENTS

| | | | |
|---|---|---|---|
| 4,252,803 | 2/1981 | Webb | 544/80 |
| 4,636,521 | 1/1987 | Coates | 514/415 |
| 4,650,810 | 3/1987 | Bays et al. | 514/415 |
| 4,672,067 | 6/1987 | Coates et al. | 514/323 |

FOREIGN PATENT DOCUMENTS

| | | | |
|---|---|---|---|
| 2082175A | 8/1981 | United Kingdom . | |
| 2168347A | 6/1986 | United Kingdom . | |
| 2185020 | 7/1987 | United Kingdom | 548/504 |

Primary Examiner—Mark L. Berch
Attorney, Agent, or Firm—Bacon & Thomas

[57] ABSTRACT

Indoles are disclosed of formula (I):

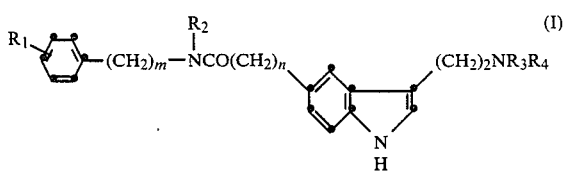

wherein
$R_1$ represents $R_5R_6NCOCH_2$—, $R_5CONH(CH_2)_p$—, $R_5R_6NSO_2(CH_2)_p$— or $R_7SO_2NH(CH_2)_p$—, (where $R_5$ and $R_6$ each represents a hydrogen atom or a $C_{1-3}$ alkyl group, $R_7$ represents $C_{1-3}$ alkyl and p is zero or one),
$R_2$ is hydrogen or $C_{1-3}$ alkyl;
$R_3$ and $R_4$ each represents hydrogen atom, $C_{1-3}$ alkyl, or 2-propenyl;
m is zero or an integer from 1 to 4; and
n is an integer from 2 to 5; and physiologically acceptable salts and solvates (e.g. hydrates) thereof.

The compounds have potent and selective vasoconstrictor activity and are indicated as useful for the treatment of migraine. They may be formulated as pharmaceutical compositions with pharmaceutically acceptable carriers of excipients for administration by any convenient route.

Various methods for the preparation of the compounds (I) are disclosed.

20 Claims, No Drawings

5-SUBSTITUTED 3-ANINOALKYL INDOLES

This invention relates to indole derivatives, to processes for their preparation, to pharmaceutical compositions containing them and to their medical use, in particular to compounds and compositions of use in the treatment of migraine.

The pain of migraine is associated with excessive dilatation of the cranial vasculature, and known treatments for migraine include the administration of compounds having vasoconstrictor properties, such as ergotamine. However, ergotamine is a non-selective vasoconstrictor which constricts blood vessels throughout the body and has undesirable and dangerous side effects. Migraine may also be treated by administering an analgesic, usually in combination with an antiemetic, but such treatments are of limited value.

There is thus a need for a safe and effective drug for the treatment of migraine, which can be used either prophylactically or to alleviate an established headache, and a compound having a selective vasoconstrictor activity would fulfil such a role.

We have now found a group of indole derivatives having potent and selective vasoconstrictor activity.

The present invention thus provides indoles of the general formula (I):

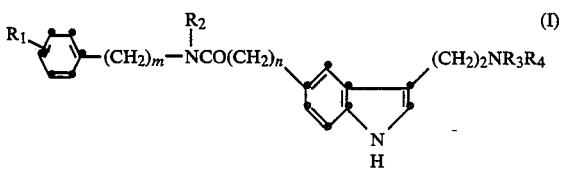

wherein $R_1$ represents a group $R_5R_6NCOCH_2$—, a group $R_5CONH(CH_2)_p$—, a group $R_5R_6NSO_2(CH_2)_p$— or a group $R_7SO_2NH(CH_2)_p$—, (where $R_5$ and $R_6$, which may be the same or different, each represents a hydrogen atom or a $C_{1-3}$ alkyl group, $R_7$ represents a $C_{1-3}$ alkyl group and p is zero or one), $R_2$ represents a hydrogen atom or a $C_{1-3}$ alkyl group;

$R_3$ and $R_4$ which may be the same or different each represents a hydrogen atom, a $C_{1-3}$ alkyl group, or a 2-propenyl group;

m is zero or an integer from 1 to 4; and n is an integer from 2 to 5; and physiologically acceptable salts and solvates (e.g. hydrates) thereof.

The invention includes within its scope all optical isomers of compounds of formula (I) and their mixtures including the racemic mixtures thereof. All geometric isomers of compounds of general formula (I) are also included within the scope of the invention.

Referring to the general formula (I), the alkyl groups may be straight chain or branched chain alkyl groups, such as methyl, ethyl or isopropyl groups.

The substituent $R_1$ may be in the ortho, meta or para position.

Suitable physiologically acceptable salts of the indoles of general formula (I) include acid addition salts formed with inorganic or organic acids, for example hydrochlorides, hydrobromides, sulphates, nitrates, oxalates, phosphates, tartrates, citrates, fumarates, maleates, succinates, and sulphonates e.g. mesylates. Other salts may be useful in the preparation of compounds of formula (I) e.g. creatinine sulphate adducts.

It will be appreciated that the invention extends to other physiologically acceptable equivalents of the compounds according to the invention, i.e. physiologically acceptable compounds which are converted in vivo into the parent compound. Examples of such equivalents include physiologically acceptable, metabolically labile N-acyl derivatives.

In the compounds of formula (I), the substituent $R^1$ may be, for example, a $CH_3CONH$—, $H_2NSO_2$— or $CH_3NHSO_2CH_2$— group or preferably a $H_2NCOCH_2$— or $CH_3SO_2NH$— group.

m may be zero or an integer 2, 3 or 4 but is preferably an integer 1.

n may be an integer 3, 4 or 5 but is preferably an integer 2.

A preferred class of compounds represented by the general formula (I) is that in which $R^2$ represents a hydrogen atom.

Another preferred class of compounds of formula (I) is that in which $R^3$ and $R^4$, which may be the same or different, each represents a hydrogen atom or a $C_{1-3}$ alkyl group, particularly a methyl or ethyl group. It is preferred that the total number of carbon atoms in $R^3$ and $R^4$ together does not exceed two. In a particularly preferred class of compounds of formula (I), $R^3$ and $R^4$ is each a methyl group.

Particularly preferred compounds of the invention are:

3-[2-(Dimethylamino)ethyl]-N-[[4-[(methylsulphonyl)amino]phenyl]methyl]-1H-indole-5-propanamide;

3-[2-(Dimethylamino)ethyl]-N-[[4-(2-amino-2-oxoethyl)phenyl]methyl]-1H-indole-5-propanamide;

and physiologically acceptable salts and solvates thereof.

Compounds of the invention selectively constrict the carotid arterial bed of the anaesthetised dog, whilst having a negligible effect on blood pressure. The selective vasoconstrictor action of compounds of the invention has been demonstrated in vitro.

Compounds of the invention are useful in treating pain resulting from dilatation of the cranial vasculature, in particular migraine and cluster headache.

Accordingly, the invention also provides a pharmaceutical composition adapted for use in human medicine which comprises at least one compound of formula (I) or a physiologically acceptable salt or solvate (e.g. hydrate) thereof and formulated for administration by any convenient route. Such compositions may be formulated in conventional manner using one or more pharmaceutically acceptable carriers or excipients.

Thus the compounds according to the invention may be formulated for oral, buccal, parenteral or rectal administration or in a form suitable for administration by inhalation or insufflation.

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium phosphate); lubricants (e.g. magnesium stearate, talc or silica); disintegrants (e.g. potato starch or sodium starch glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, methyl cellulose or hydrogenated edible fats); emulsifying agents (e.g. lecithin or acacia); non-aqueous vehicles (e.g. almond oil, oily esters or ethyl alcohol); and preservatives (e.g. methyl or propyl-p-hydroxybenzoates or sorbic acid). The liquid preparations may also contain conventional buffers, flavouring, colouring and sweetening agents as appropriate.

For buccal administration the compositions may take the form of tablets or lozenges formulated in conventional manner.

The compounds of the invention may be formulated for parenteral administration by injection or continuous infusion. Formulations for injection may be presented in unit dosage form e.g. in ampoules or in multi-dose containers, with an added preservative.

The compositions may take such forms as suspensions, solutions or emulsions in oily or aqueous vehicles, and may contain formulatory agents such as suspending, stabilising and/or dispersing agents, and/or agents to adjust the tonicity of the solution. Alternatively, the active ingredient may be in powder form for constitution with a suitable vehicle, e.g. sterile pyrogen-free water, before use.

The compounds of the invention may also be formulated in rectal compositions such as suppositories or retention enemas, e.g. containing conventional suppository bases such as cocoa butter or other glycerides.

For administration by inhalation according to the invention are conveniently delivered in the form of an aerosol spray presentation from pressurised packs, with the use of a suitable propellant, e.g. dichlorodifluoromethane, trichlorofluoromethane, dichlorotetrafluoroethane, carbon dioxide or other suitable gas, or from a nebuliser. In the case of a pressurised aerosol the dosage unit may be determined by providing a valve to deliver a metered amount. Capsules and cartridges of e.g. gelatin for use in an inhaler or insufflator may be formulated containing a powder mix of a compound of the invention and a suitable powder base such as lactose or starch.

A proposed dose of the compounds of the invention for oral, parenteral, buccal or rectal administration to man (of average bodyweight e.g. about 70 kg) for the treatment of migraine is 0.1 to 100 mg of the active ingredient per unit dose which could be administered, for example, up to 8 times per day, more usually 1 to 4 times per day. It will be appreciated that it may be necessary to make routine variations to the dosage depending on the age and weight of the patient as well as the severity of the condition to be treated.

For oral administration a unit dose will preferably contain from 0.5 to 50 mg e.g. 2 to 40 mg of the active ingredient. A unit dose for parenteral administration will preferably contain 0.2 to 5 mg of the active ingredient.

Aerosol formulations are preferably arranged so that each metered dose or 'puff' delivered from a pressurised aerosol contains 0.2 to 2 mg of a compound of the invention and, each dose administered via capsules or cartridges in an inhaler or insufflator contains 0.2 to 20 mg. The overall daily dose by inhalation will be within the range 1 mg to 100 mg. Administration may be several times daily, for example from 2 to 8 times, giving for example 1, 2 or 3 doses each time.

The compounds of the invention may, if desired, be administered in combination with one or more other therapeutic agents, such as analgesics, anti-inflammatory agents and anti-nauseants.

According to another aspect of the invention, compounds of formula (I), and physiologically acceptable salts or solvates (e.g. hydrates) thereof, may be prepared by the general methods outlined below. In the following processes, $R_1$, $R_2$, $R_3$, $R_4$, m and n are as defined for the general formula (I) unless otherwise specified.

According to one general process (A), a compound of general formula (I) may be prepared by condensing an amine of formula (II):

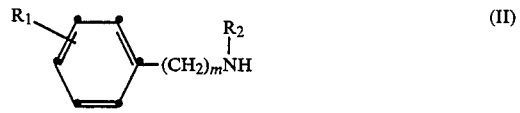

with an acid of general formula (III):

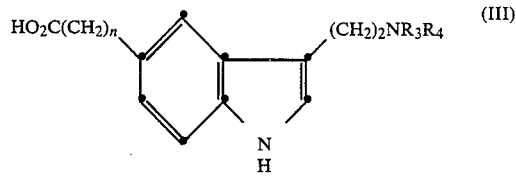

or an acylating agent corresponding thereto, or a salt (for example an organic or inorganic acid addition salt such as the hydrochloride, hydrobromide, sulphate or maleate salt, or creatinine sulphate adduct) or a protected derivative thereof.

The reaction involving condensation of the amine of formula (II) with the acid of general formula (III) is desirably conducted in the presence of a coupling agent, for example carbonyl diimidazole or a carbodiimide such as N,N'-dicyclohexylcarbodiimide. The condensation reaction may be carried out in a suitable reaction medium preferably an anhydrous medium, conveniently at a temperature of from $-50°$ to $+50°$ C., preferably $-5°$ to $+30°$ C. Suitable solvents include halogenated hydrocarbons e.g. dichloromethane, nitriles e.g. acetonitrile, amides e.g. N,N-dimethylformamide and ethers e.g. tetrahydrofuran, as well as mixtures of two or more such solvents. The reaction may also be carried out in the absence of a coupling agent in a suitable reaction medium such as a hydrocarbon (e.g. toluene or xylene) conveniently at a temperature of from 50° to 120° C.

Acylating agents corresponding to the acid of general formula (III) which may be employed in the preparation of compounds of formula (I) include acid halides, for example acid chlorides. Such acylating agents may be prepared by reaction of an acid of general formula (III), or a salt or protected derivative thereof, with a halogenating agent such as phosphorus pentachloride, thionyl chloride or oxalyl chloride. Other suitable acylating agents which may be employed in the preparation of compounds of formula (I) include alkyl esters such as the methyl ester, activated esters (e.g. the 2-(1-methylpyridinyl)ester) and mixed anhydrides (e.g. formed with pivaloyl chloride, a sulphonyl halide such as methanesulphonyl chloride or a haloformate, such as a lower alkylhaloformate). Acids of formula (III) may themselves be prepared for example by cyclisation of an appropriate hydrazine compound, in an analogous manner to process (B) described hereinafter.

When an acylating agent corresponding to the acid of general formula (III) is employed the condensation process may be effected in aqueous or non-aqueous reaction media and conveniently at a temperature of from −70° to −150° C. Thus the condensation reaction using an acid halide, anhydride or activated ester may be effected in a suitable reaction medium such as an amide e.g. N,N-dimethylformamide, an ether e.g. tetrahydrofuran or diethylether, a nitrile e.g. acetonitrile, a halogenated hydrocarbon e.g. dichloromethane, or mixtures thereof, optionally in the presence of a base such as a tertiary amine e.g. triethylamine or pyridine and preferably at a temperature of from −5° to +25° C. The condensation reaction using an alkyl ester may be effected in a suitable reaction medium such as an alcohol e.g. methanol, an amide e.g. dimethylformamide, an ether e.g. tetrahydrofuran or diethylether, or mixtures thereof and conveniently at a temperature of from 0° to 100° C. In some instances, the amine of formula (II) may itself act as the reaction solvent.

According to a further general process (B) compounds of general formula (I) wherein $R_1$ represents a group $R_5CONH(CH_2)_p-$ may be prepared by reacting a compound of general formula (IV):

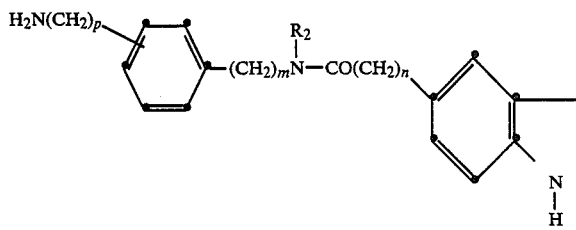

with an acid of formula $R^5COOH$, or with an acylating derivative thereof.

Acylating derivatives of the acid $R^5COOH$ which may be employed in general process (B), include acid halides, e.g. acid chlorides; mixed anhydrides; alkyl esters; and activated esters, e.g. the 2-(1-methylpyridinyl) ester; as described previously for general process (A). The acylation reaction with an acid of formula $R^5COOH$ or an acylating derivative thereof may be effected using similar reaction conditions to those described above for general process (A).

Compounds of general formula (IV) may be prepared by reduction of a compound of general formula (V):

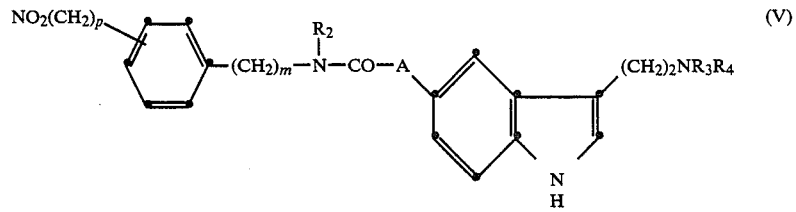

wherein A represents a $C_{2-5}$ alkenyl group.

The reduction may be effected for example with hydrogen in the presence of a metal catalyst. Suitable catalysts and reaction conditions are described in more detail in general process (E) hereinafter.

Compounds of general formula (V) may be prepared by reacting an aldehyde of general formula (VI):

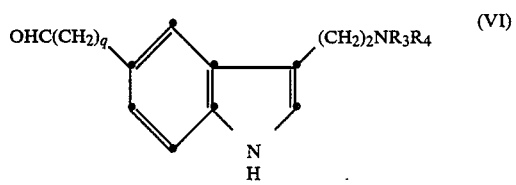

(wherein q is zero or an integer of from 1 to 3) with, for example, an appropriate phosphonium salt. Alternatively, compounds of general formula (V) may be prepared by reacting an indole of general formula (VII):

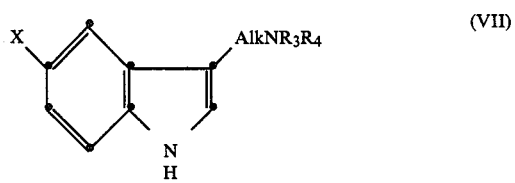

(wherein X represents a halogen atom, e.g. a bromine or iodine atom) with an alkene of formula (VIII):

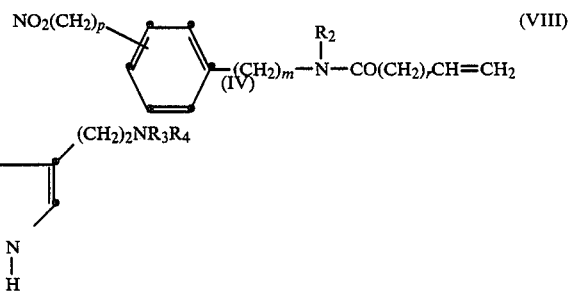

(wherein r represents an integer from 1 to 3).

The reaction will generally be effected in the presence of a palladium catalyst and a base. The catalyst may be for example palladium on charcoal or a palladium salt. Palladium salts which may be employed as catalysts include salts of organic acids, e.g. acetates, and salts of inorganic acids e.g. chlorides or bromides. The base may be for example a tertiary nitrogen base such as triethylamine or tri-n-butylamine, or an alkali metal carbonate, e.g. sodium carbonate. The reaction may optionally be carried out in the presence of a phosphine, for example a triarylphosphine such as triphenylphosphine or tri-o-tolylphosphine. A phosphine should be present when the process is effected with a compound of formula (VII) wherein X represents a bromine atom.

The compounds of formula (VIII) may be prepared for example by condensing the appropriate amine e.g. p-nitrobenzylamine with the appropriate acid chloride e.g. acryloyl chloride, using standard conditions.

According to another general process (C), compounds of formula (I) may be prepared by the cyclisation of a compound of general formula (IX):

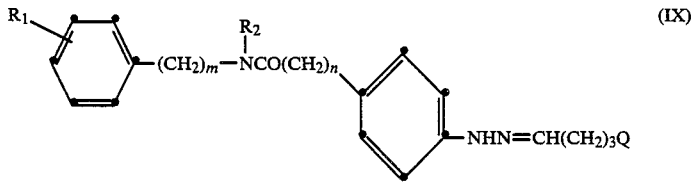

wherein Q is the group $NR_3R_4$ (or a protected derivative thereof) or a leaving group such as a halogen atom (e.g. chlorine or bromine) or an acyloxy group (e.g. a carboxylic or sulphonic acyloxy group such as an acetoxy, chloroacetoxy, dichloroacetoxy, trifluoroacetoxy, p-nitrobenzoyloxy, p-toluenesulphonyloxy or methanesulphonyloxy group).

The reaction may conveniently be effected in aqueous or non-aqueous reaction media, and at temperatures of from 20° to 200° C., preferably 50° to 125° C.

Particularly convenient embodiments of the process are described below.

When Q is the group $NR_3R_4$ (or a protected derivative thereof) the process is desirably carried out in the presence of polyphosphate ester in a reaction medium which may comprise one or more organic solvents, preferably halogenated hydrocarbons such as chloroform, dichloromethane, dichloroethane, dichlorodifluoromethane, or mixtures thereof. Polyphosphate ester is a mixture of esters which may be prepared from phosphorus pentoxide, diethylether and chloroform according to the method described in 'Reagents for Organic Synthesis', (Fieser and Fieser, John Wiley and Sons 1967).

Alternatively the cyclisation may be carried out in an aqueous or non-aqueous reaction medium, in the presence of an acid catalyst. When an aqueous medium is employed this may be an aqueous organic solvent such as an aqueous alcohol (e.g. methanol, ethanol or isopropanol) or an aqueous ether (e.g. dioxan or tetrahydrofuran) as well as mixtures of such solvents, and the acid catalyst may be for example, an inorganic acid such as concentrated hydrochloric or sulphuric acid or an organic acid, such as acetic acid. (In some cases the acid catalyst may also act as the reaction solvent). In an anhydrous reaction medium, which may comprise one or more ethers (e.g. as previously described) or esters (e.g. ethyl acetate), the acid catalyst will generally be a Lewis acid such as boron trifluoride, zinc chloride or magnesium chloride.

When Q is a leaving group such as a chlorine or bromine atom the reaction may be effected in an aqueous organic solvent, such as an aqueous alcohol (e.g. methanol, ethanol or isopropanol) or an aqueous ether (e.g. dioxan or tetrahydrofuran) in the absence of an acid catalyst, conveniently at a temperature of from 20° to 200° C., preferably 50° to 125° C. This process results in the formation of a compound of formula (I) wherein $R_3$ and $R_4$ are both hydrogen atoms.

According to a particular embodiment of this process compounds of formula (I) may be prepared directly by the reaction of a compound of general formula (X):

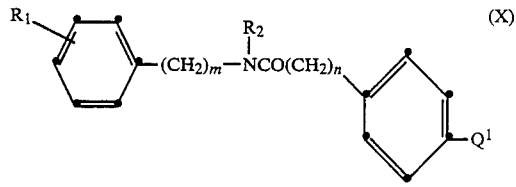

(where $Q^1$ is a group —$NHNH_2$) or a salt thereof, with a compound of formula (XI):

$$OHC(CH_2)_3Q \qquad (XI)$$

(wherein Q is as defined above) or a salt or protected derivative thereof (such as an acetal or ketal e.g. formed with an appropriate alkyl orthoformate or diol, or protected as a bisulphite addition complex) using the appropriate conditions as described above for the cyclisation of compounds of general formula (IX). It will be appreciated that this embodiment of the cyclisation process (C) a compound of general formula (IX) is formed as an intermediate, and may be reacted in situ to form the desired compound of general formula (I).

Compounds of general formula (IX) may, if desired, be isolated as intermediates during the process for the preparation of compounds of formula (I) wherein a compound of formula (X), or a salt or protected derivative thereof, is reacted with a compound of formula (XI), or a salt or protected derivative thereof, in a suitable solvent, such as an aqueous alcohol (e.g. methanol) at a temperature of, for example, 20° to 30° C. If an acetal or ketal of a compound of formula (XI) is used, it may be necessary to carry out the reaction in the presence of an acid (for example, acetic or hydrochloric acid).

Compounds of general formula (X) may be prepared for example from the corresponding nitro compounds, (in which $Q^1$ is —$NO_2$) using conventional procedures.

A further general process (D) for preparing compounds of general formula (I) involves reacting a compound of general formula (XII):

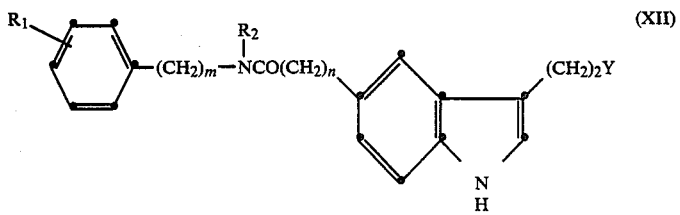

(XII)

(wherein Y is a readily displaceable group) or a protected derivative thereof, with an amine of formula $R_3R_4NH$.

The displacement reaction may conveniently be carried out on those compounds of formula (XII) wherein the substituent group Y is a halogen atom (e.g. chlorine, bromine or iodine) or a group $OR_8$ where $OR_8$ is, for example, an acyloxy group which may be derived from a carboxylic or sulphonic acid, such as an acetoxy, chloroacetoxy, dichloroacetoxy, trifluoroacetoxy, p-nitrobenzoyloxy, p-toluenesulphonyloxy or methanesulphonyloxy group.

The displacement reaction may be conveniently effected in an inert organic solvent (optionally in the presence of water), examples of which include alcohols, e.g. ethanol; cyclic ethers, e.g. dioxan or tetrahydrofuran; acrylic ethers e.g. diethylether; esters, e.g. ethyl acetate; amides, e.g. N,N-dimethylformamide; and ketones e.g. acetone or methylethyl ketone, at a temperature of from $-10°$ to $+150°$ C., preferably 20° to 50° C.

The compounds of general formula (XII) wherein Y is a halogen atom may be prepared by reacting a hydrazine of general formula (X) with an aldehyde or ketone (or a protected derivative thereof) of formula (XI) in which Q is a halogen atom, in an aqueous alkanol (e.g. methanol) containing an acid (e.g. acetic or hydrochloric acid). Alternatively, compounds of formula (XII) wherein Y is a halogen atom may be prepared from the corresponding compounds werein Y is a hydroxyl group by halogenation with an appropriate halogenating agent, for example, phosphorus tribromide, using conventional techniques. Compounds of formula (XII) wherein Y is the group $OR_8$ may be prepared from the corresponding compound wherein Y is a hydroxyl group by acylation or sulphonylation with the appropriate activated species (e.g. anhydride or sulphonyl chloride) using conventional techniques. The intermediate alcohol may be prepared by cyclisation of a compound of formula (IX) wherein Q is a hydroxyl group (or a protected derivative thereof) under standard conditions.

Compounds of formula (I) may also be prepared by another general process (E) involving reduction of a compound of general formula (XIII):

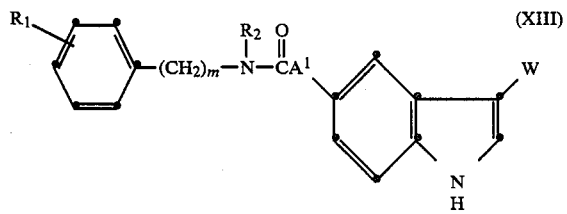

(XIII)

[wherein W is a group capable of being reduced to give the required $-(CH_2)_2NR_3R_4$ group or a protected derivative thereof and $A^1$ represents the group $-(CH_2)_n-$ as herein defined or a group capable of being reduced to $-(CH_2)_n-$] or a salt or protected derivative thereof.

The required $-(CH_2)_2-$ and $-NR_3R_4$ groups at the 3-position may be formed by reduction steps which take place separately or together in any appropriate manner.

Groups $A^1$ which may be reduced to give the required group $-(CH_2)_n-$ include $C_{2-5}$ alkenyl or $C_{2-5}$ alkynyl groups.

Examples of groups represented by the substituent W include $-(CH_2)_2NO_2$; $-CH=CHNO_2$; $-(CH_2)_2N_3$; $-CH_2CN$; $-CH_2CHO$; $-COCH_2Z$; $-CH_2CH=NOH$; and $-CH(OH)CH_2NR_3R_4$; (wherein Z is an azido group or the group $-NR_3R_4$ or a protected derivative thereof).

Groups whch may be reduced to the $-(CH_2)_2-$ moiety at the 3-position include the corresponding unsaturated group and corresponding groups containing a hydroxyl group or a carbonyl function.

Groups which may be reduced to the group $-NR_3R_4$ where $R_3$ and $R_4$ are both hydrogen include nitro, azido, hydroxyimino and nitrile groups. In the latter case, reduction yields the group $-CH_2NH_2$ and thus provides a methylene group of the $-(CH_2)_2-$ moiety.

The required $-NR_3R_4$ group wherein $R_3$ and/or $R;hd 4$ are other than hydrogen may be prepared by reduction of a nitrile $-CH_2CN$ or an aldehyde $-CH_2CHO$ in the presence of an amine, $R_3R_4NH$.

A particularly suitable method for preparing a compound of formula (I) wherein $R_3$ and/or $R_4$ is other than hydrogen is reductive alkylation of the corresponding compound wherein $R_3$ and/or $R_4$ represent hydrogen with an appropriate aldehyde or ketone (e.g. formaldehyde or acetone) in the presence of a suitable reducing agent. In some instances (e.g. for the introduction of the group(s) $R_3$ and/or $R_4$ where these represent methyl) the aldehyde (e.g. formaldehyde) may be condensed with the amine and the intermediate thus formed may subsequently be reduced using a suitable reducing agent.

It will be appreciated that the choice of reducing agent and reaction conditions will be dependent on the nature of the group W, as well as the other groups already present on the molecule.

Suitable reducing agents which may be used in the above process for the reduction of compounds of formula (XIII) wherein W represents, for example, the groups $-(CH_2)_2NO_2$, $-CH=CHNO_2$, $-(CH_2)_2N_3$, $-CH_2CN$, $-CH_2CH=NOH$ and $-CH(OH)CH_2NR_3R_4$ include hydrogen in the presence of a metal catalyst, for example Raney Nickel or a noble metal catalyst such as platinum, platinum oxide, palladium, palladium oxide or rhodium, which may be supported, for example, on charcoal, kieselguhr or alumina. In the case of Raney Nickel, hydrazine may also be used as the source of hydrogen. This process may conveniently be carried out in a solvent such as an alcohol e.g.

ethanol, an ether, e.g. dioxan or tetrahydrofuran, an amide, e.g. dimethylformamide or an ester e.g. ethyl acetate, and at a temperature of from −10° to +50° C., preferably −5° to +30° C.

The reduction process may also be effected on compounds of formula (XIII) wherein W represents, for example, the groups —(CH$_2$)$_2$NO$_2$, —CH=CHNO$_2$, —(CH$_2$)$_2$N$_3$, —CH(OH)CH$_2$NR$_3$R$_4$ or —COCH$_2$Z (where Z is as previously defined), using an alkali metal or alkaline earth metal borohydride or cyanoborohydride e.g. sodium or calcium borohydride or cyanoborohydride which process may conveniently be carried out in an alcohol such as propanol or ethanol, or a nitrile such as acetonitrile, and at a temperature of from 10° to 100° C., preferably 50° to 100° C. In some instances the reduction using a borohydride may be carried out in the presence of cobaltous chloride.

Reductive alkylation of a compound of formula (XIII) may be effected using an alkali metal or alkaline earth metal borohydride or cyanoborohydride. The reaction may be effected in an aqueous or nonaqueous reaction medium, conveniently in an alcohol (e.g. methanol or ethanol) or an ether (e.g. dioxan or tetrahydrofuran) optionally in the presence of water. The reaction may conveniently be carried out at a temperature in the range of 0° to 100° C., preferably 5° to 50° C.

A particular embodiment of general process (E) includes the reduction of a compound of formula (XIII) wherein W is the group —CH$_2$CN, for example by catalytic reduction with hydrogen in the presence of a catalyst such as palladium on charcoal or rhodium on alumina, optionally in the presence of an amine HNR$_3$R$_4$. The reduction may be effected in a suitable solvent such as an alcohol e.g. methanol or ethanol.

A compound of general formula (I) where R$_4$ is a hydrogen atom may also be prepared by hydrogenolysis of a corresponding compound wherein R$_4$ is a benzyl group, e.g. with hydrogen in the presence of a catalyst, e.g. 10% palladium on carbon.

Suitable reducing agents which may be used in the reduction of the group A$^1$ include hydrogen in the presence of a metal catalyst. Appropriate metal catalysts and conditions or the reduction process are as described for the reduction of the group W.

The starting materials or intermediate compounds of formula (XIII) wherein W represents —(CH$_2$)$_2$NO$_2$, —CH=CHNO$_2$, —CH$_2$CN or —COCH$_2$Z may be prepared by analogous methods to those described in UK Published Patent Application No. 2035310, and 'A Chemisry of Heterocyclic Compounds—Indoles Part II', Chapter VI, edited by W J Houlihan (1972) Wiley Interscience, New York.

Compounds of formula (XIII), wherein W is the group —CH$_2$CHO may be prepared by oxidation (e.g. with Jones' reagent) of a compound of formula (XII) wherein Y is a hydroxyl group. A compound of formula (XIII) wherein W is the group —CH$_2$CH=NOH may be prepared by treatment of the corresponding aldehyde with hydroxylamine hydrochloride using standard conditions.

The intermediate compound of formula (XIII) wherein W is the group —(CH$_2$)$_2$N$_3$ may be prepared from a compound of formula (XII) wherein Y is a halogen atom using standard procedures.

Standard reducing agents such as sodium borohydrode may be used to prepare a compound of formula (XIII) wherein W is the group —CH(OH)CH$_2$NR$_3$R$_4$ from the corresponding compound of formula (XIII) wherein W is the group —COCH$_2$NR$_3$R$_4$.

The intermediate compounds of formula (XIII) wherein A$^1$ represents a C$_{2-5}$ alkenyl group may be prepared by reacting a compound of general formula (XIV):

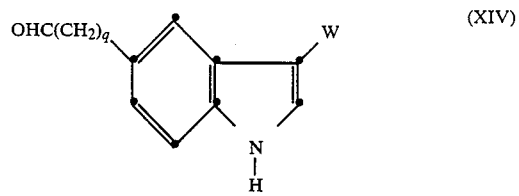

(wherein W is as defined for general formula (XIII) and q is zero or an integer of from 1 to 3) with, for example, an appropriate phosphonium salt, using standard conditions.

According to a further general process (F) compounds of general formula (I) wherein R$^1$ represents a group R$^5$R$^6$NCOCH$_2$— may be prepared by reacting an amine of formula R$^5$R$^6$NH with an acid of formula (XV):

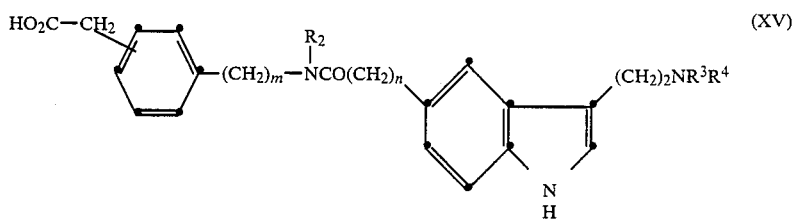

or an acylating agent corresponding thereto, or a salt or a protected derivative thereof.

Acylating derivatives of the acid which may be used in the general process (F) include acid halides; mixed anhydrides, alkyl esters such as the methyl or ethyl ester and activated esters as described previously for general process (A). The acylation reaction with the acid of formula (XV) or an acylating derivative thereof may be effected using similar reaction conditions to those described for general process (A).

Compounds of general formula (XV) may be prepared by reduction of a compound of general formula (XVI):

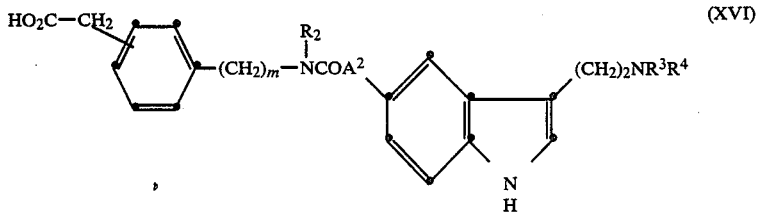

wherein $A^2$ represents a $C_{2-5}$ alkenyl group, or a salt or protected derivative thereof.

The reduction may be effected, for example, with hydrogen in the presence of a metal catalyst. Suitable catalyst and reduction conditions are those described in process (E) above.

Compounds of general formula (XVI) may be prepared, for example, by reacting an aldehyde of general formula (VI) with an appropriate phosphonium salt using standard conditions. Alternatively, compounds of general formula (XVI) may be prepared, for example, by reacting an indole of general formula (VII) with an alkene of formula (XVII):

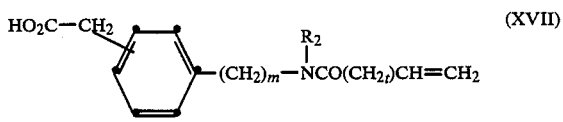

(wherein t represents an integer from 1 to 3).

The reaction may be effected using similar conditions to those described for the preparation of compounds of formula (VIII) in general process (B).

Compounds of general formula (XVII) may be prepared from the appropriate amine, for example ethyl 4-(aminomethyl)benzene-acetate and the appropriate acid chloride, for example, acryloyl chloride, using conventional procedures.

According to a further general process (G) a compound of formula (I) according to the invention, or a salt or protected derivative thereof, may be converted into another compound of formula (I) using conventional procedures.

For example, a compound of general formula (I) wherein one or more of $R_2$, $R_3$ and $R_4$ are alkyl groups may be prepared from the corresponding compounds of formula (I) wherein one or more of $R_2$, $R_3$ and $R_4$ represent hydrogen atoms, by reaction with a suitable alkylating agent such as a compound of formula $R_xL$, (where $R_x$ represents the desired $R_2$, $R_3$ or $R_4$ group and L represents a leaving group such as a halogen atom or a tosylate group) or a sulphate $(R_x)_2SO_4$. Thus, the alkylating agent may be for example an alkyl halide (e.g. methyl or ethyl iodide), alkyl tosylate (e.g. methyl tosylate) or dialkylsulphate (e.g. dimethylsulphate).

The alkylation reaction may conveniently be carried out in an inert organic solvent such as an amide (e.g. dimethylformamide), an ether (e.g. tetrahydrofuran) or an aromatic hydrocarbon (e.g. toluene) preferably in the presence of a base. Suitable bases include, for example, alkali metal hydrides such as sodium or potassium hydride; alkali metal amides such as sodium amide; alkali metal carbonates such as sodium carbonate; alkali metal alkoxides such as sodium or potassium methoxide, ethoxide or t-butoxide; and tetrabutylammonium fluoride. When an alkyl halide is employed as the alkylating agent the reaction may also be carried out in the presence of an acid scavenging agent such as propylene or ethylene oxide. The reaction may be conveniently effected at a temperature of from $-20°$ to $100°$ C.

Compounds of formula (I) wherein one or both of $R_3$ and $R_4$ represents propenyl may be prepared similarly, using an appropriate compound of formula $R_xL$ or $(R_x)_2SO_4$.

According to another general process (H), a compound of general formula (I) according to the invention, or a salt thereof may be prepared by subjecting a protected derivative of general formula (I) or a salt thereof to reaction to remove the protecting group or groups.

Thus, at an earlier stage in the reaction sequence for the preparation of a compound of general formula (I) or a salt thereof it may have been necessary or desirable to protect one or more sensitive groups in the molecule to avoid undesirable side reactions. For example it may be necessary to protect the group $NR_3R_4$, wherein $R_3$ and/or $R_4$ represents hydrogen, by protonation or with a group easily removable at the end of the reaction sequence. Such groups may include, for example, aralkyl groups, such as benzyl, diphenylmethyl or triphenylmethyl; or acyl groups such as N-benzyloxycarbonyl or t-butoxycarbonyl or phthaloyl.

In some cases, it may also be desirable to protect the indole nitrogen with, for example, an aralkyl group such as benzyl.

Subsequent cleavage of the protecting group or groups may be achieved by conventional procedures. Thus an aralkyl group such as benzyl, may be cleaved by hydrogenolysis in the presence of a catalyst (e.g. palladium on charcoal) or sodium and liquid ammonia; an acyl group such as N-benzyloxycarbonyl may be removed by hydrolysis with, for example, hydrogen bromide in acetic acid or by reduction, for example by catalytic hydrogenation. The phthaloyl group may be removed by hydrazinolysis (e.g. by treatment with hydrazine hydrate) or by treatment with a primary amine (e.g. methylamine).

As will be appreciated, in some of the general processes (A) to (G) described previously it may be necessary or desirable to protect any sensitive groups in the molecule as just described. Thus, a reaction step involving deprotection of a protected derivative of general formula (I) or a salt thereof may be carried out subsequent to any of the previously described processes (A) to (G).

Thus, according to a further aspect of the invention, the following reactions in any appropriate sequence may if necessary and/or desired be carried out subsequent to any of the processes (A) to (G):

(i) removal of any protecting groups; and
(ii) conversion of a compound of general formula (I) or a salt thereof into a physiologically acceptable salt or solvate (e.g. hydrate) thereof.

Where it is desired to isolate a compound of the invention as a salt, for example as an acid addition salt, this may be achieved by treating the free base of general formula (I), with an appropriate acid, preferably with an equivalent amount, or with creatinine sulphate in a suitable solvent (e.g. aqueous ethanol).

The starting materials or intermediate compounds for the preparation of the compounds according to this invention may be prepared by analogous methods to those described in UK Published Patent Application No. 2035310.

As well as being employed as the last main step in the preparative sequence, the general methods indicated above for the preparation of the compounds of the invention may also be used for the introduction of the desired groups at an intermediate stage in the preparation of the required compound. Thus, for example, the required group at the 5-position may be introduced before or after cyclisation to form the indole nucleus. It should therefore be appreciated that in such multi-stage processes, the sequence of reactions should be chosen in order that the reaction conditions do not affect groups present in the molecule which are desired in the final product.

The invention is further illustrated by the following Examples. All temperatures are in °C.

Chromatography was carried out either in the conventional manner using silica gel (Merck, Kieselgel 60, Art. 7734) or by flash chromatography on silica (Merck 9385) and thin-layer chromatography (t.l.c.) on silica (Macherly-Nagel, Polygram) except where otherwise stated.

The following abbreviations define the eluants used for column chromatography and t.l.c.:
(A) Methylene chloride-ethanol-0.88 ammonia 100:8:1
(B) Methylene chloride-ethanol-0.88 ammonia 25:8:1
(C) Ethyl acetate
(D) Methylene chloride-ethanol-0.88 ammonia 50:8:1
(E) Ether-isopropanol-water-0.88 ammonia 20:20:8:1
(F) Cyclohexane
(G) Methylene chloride
(H) Ether
(I) Methylene chloride-ethanol-0.88 ammonia 250:8:1

Proton ($^1$H) nuclear magnetic resonance (n.m.r.) spectra were obtained either at 90 MHz using a Varian EM 390 instrument or at 250 MHz using a Bruker AM or WM 250 instrument, s=singlet, d=doublet, t=triplet, m=multiplet and q=quartet. Chemical shift values, δ, are measured in parts per million (p.p.m.) N.m.r. spectra were run in deuterated dimethylsulphoxide as solvent unless otherwise indicated.

INTERMEDIATE 1

N-(4-Nitrophenylmethyl)-2-propenamide

A solution of freshly prepared 4-nitrobenzylamine (3.8 g) in dry dichloromethane (100 ml) containing triethylamine (3.5 ml) was added dropwise to acryloyl chloride (2.2 ml) in dry dichloromethane (100 ml), over 20 min during which time the temperature was kept between −15° and −7°. The reaction mixture was stirred at this temperature for 0.5 h. and then allowed to reach room temperature over a period of 1.25 h. The resulting solution was washed with 2N hydrochloric acid (50 ml), water (50 ml), aqueous 8% sodium bicarbonate solution, and water (50 ml), dried (MgSO$_4$) and evaporated to dryness to afford a solid (3.89 g). This which was triturated with cyclohexane (about 400 ml) to give the title compound as a powder (3.654 g) m.p. 119°–121°.

INTERMEDIATE 2

E-3-[3-[2-(Dimethylamino)ethyl]-1H-indol-5-yl]-N-[(4-nitrophenyl)-methyl]-2-propenamide A mixture of 5-iodo-N,N-dimethyl-1H-indole-3-ethanamine (1.36 g), Intermediate 1 (1.0 g), palladium acetate (37.5 mg) and triethylamine (1.0 ml) in acetonitrile (3 ml) was heated at 115°–120° in a reactivial for 1 h. The cooled mixture was absorbed onto silica, the solvent evaporated and the product was purified by flash chromatography (A). Evaporation of the appropriate fractions afforded a gum (0.32 g), which was further purified by flash chromatography to give a solid. This was triturated with either to give the title compound as a powder (0.21 g) m.p. 177°–187°.

INTERMEDIATE 3

N-[(4-aminophenyl)methyl]-3-[2-(Dimethylamino)ethyl]-1H-indole-5-propanamide dihydrochloride A solution of the Intermediate 2 (0.96 g) in ethanol (160 ml) was added to a slurry of pre-reduced 10% palladium oxide on carbon (2.5 g of a 50% aqueous paste) in ethanol (50 ml) and the mixture stirred rapidly under hydrogen at atmospheric pressure and temperature, until hydrogen absorption ceased after 1.25 h. The catalyst and solvent were removed by filtration and rotary evaporation respectively, to afford a foam which was purified by flash chromatography (D). Evaporation of the appropriate fractions gave the title compound free base as a gum (0.43 g) which was dissolved in ethanol (10 ml) and treated with excess ethereal hydrogen chloride. The mixture was evaporated to dryness to yield a foam (0.548 g) which was triturated with anhydrous ether to give the title compound as a powder (0.39 g). T.l.c. (B) Rf 0.5.

INTERMEDIATE 4

Ethyl 4-[[(1-oxo-2-propenyl)amino]methyl]benzeneacetate

A solution of Ethyl 4-[aminomethyl]benzeneacetate (4.12 g) in anhydrous dichloromethane (60 ml) containing triethylamine (3.0 ml), was added over 20 min to a cold (−15°) stirred solution of acryloyl chloride (1.73 ml) in dry dichloromethane (50 ml) and stirring was continued for 0.75 h. After washing the dichloromethane solution with 8% aqueous sodium bicarbonate soln (2×50 ml) and drying (MgSO$_4$), the organic solvent was removed by rotary evaporation to yield a a solid (approximately 6 g) which was triturated with cyclohexane to give the title compound as a solid (4.1 g) m.p. 93°–95°.

INTERMEDIATE 5

3-[2-(Dimethylamino)ethyl]-1H-indole-5-propanoic acid

A mixture of Methyl 3-[2-(Dimethylamino)ethyl]-1H-indole-5-propanoate (4.6 g) and lithium hydroxide hydrate (0.7 g) in aqueous methanol (1:1) (80 ml) was stirred under reflux for 4.5 h. The solvent was removed by evaporation to leave a foam which was purified by flash chromatography (E). Evaporation of the appropriate fractions gave a solid which was triturated with ether to present the title compound as a powder (2.92 g) m.p. 195°–200°.

INTERMEDIATE 6

(E)-Ethyl-4[[[3-[3-[2-(Dimethylamino)ethyl]-1H-indol-5-yl]-1-oxo-2-propenyl]amino]methyl]benzeneacetate, hemisuccinate A mixture of 5-iodo-N,N-dimethyl-1H-indole-3-ethanamine oxalate (1.0 g), Intermediate 4 (0.612 g), a palladium acetate (28 mg), triethylamine (2.0 ml) and acetonitrile (6 ml) was heated with stirring in a 'reactivial' at 115° for 3 h. The mixture was evaporated to dryness and the residual gum purified by chromatography (A) to give the free base as a foam (0.87 g) on evaporation of the appropriate fractions. A hot solution of the free base (0.3 g) in isopropanol (3 ml) was treated with a hot solution of succinic acid (0.0819 g) in hot isopropanol (1.5 ml) and the solution was evaporated to dryness. The residual foam was triturated with anhydrous ether to present the title compound as a solid (0.275 g) m.p. 60°–65°.

INTERMEDIATE 7

Ethyl-4-[[[3-[3-[2-(dimethylamino)ethyl]-1H-indol-5-yl]-1-oxopropyl]amino]methyl]benzeneacetate hemisuccinate A solution of Intermediate 6 (0.59 g) in alcohol (55 ml) was hydrogenated in the presence of pre-reduced 10% palladium oxide on carbon (0.5 g of a 50% paste in water) at room temperature and atmospheric pressure. Uptake of hydrogen ceased after 18 h. The catalyst and solvent were removed by filtration and rotary evaporation respectively to give a cream foam (0.5 g) which was purified by flash chromatography (B) to give the title compound free base as a gum (0.15 g). A solution of the free base (89 mg) in hot isopropanol (1 ml) was treated with a hot solution of succinic acid (12.1 mg) in isopropanol (1 ml) and the resulting mixture was dissolved in methanol and evaporated to yield a sticky gum. This material was stirred with anhydrous ether to give the title salt as a hygroscopic solid (57 mg) m.p. 45°–50°.

INTERMEDIATE 8

(E) Ethyl 4-[[[[3-(cyanomethyl)-1H-indol-5-yl]-1-oxo-2-propenyl-]amino]methyl]benzeneacetate A mixture of 5-bromo-3-cyanomethyl-1H-indole (0.5 g) Intermediate 4 (0.526 g) with palladium acetate (0.019 g) tri-(orthotolyl)phosphine (0.038 g) triethylamine (1.0 ml) and acetonitrile (4 ml) was heated in a sealed "Reactivial" with stirring at 115° (oil bath temp) for 20 h. The cooled reaction mixture was chromatographed using flash chromatography (G,H) and the appropriate fractions evaporated to produce a solid (0.37 g), which was further purified by flash chromatography (I). Evaporation of the appropriate fractions gave a gum which solidified to give the title compound as a solid (0.18 g) m.p. 125°–130°.

INTERMEDIATE 9

Ethyl 4-[[[[3-(cyanomethyl)-1H-indol-5-yl]-1-oxo-2-propyl-]amino]methyl]benzeneacetate A solution of Intermediate 8 (2.63 g) in ethanol (100 ml) was hydrogenated in the presence of 10% palladium oxide on carbon [1.0 g of a 50% paste in water, pre-reduced in ethanol (50 ml)] at room temperature and atmospheric pressure for 20 h. Removal of the catalyst and solvent in the normal manner gave the title compound as a viscous gum (2.4 g). T.l.c. SiO$_2$ (A) Rf 0.5 u.v.

INTERMEDIATE 10

N-[[4-(2-Amino-2-oxoethyl)phenyl]methyl]-3-(cyanomethyl)-1H-indole propanamide

A solution of Intermediate 9 (0.58 g) in ethanol (10 ml) was treated with 0.88-ammonia solution (10 ml) and the resultant solution stirred at room temperature for 20 h. More ammonia solution (5 ml) was added and after another 3 h a further portion (3 ml) was added before stirring at room temperature for 72 h. The solution was evaporated to dryness to give a foam (0.6 g) which was purified by flash chromatography (A) and evaporation to give the title compound as a powder (0.152 g) m.p. 130°–140°.

EXAMPLE 1

3-[2-(Dimethylamino)ethyl]-N-[[4-(acetylamino)-phenyl]methyl]-1H-indole-5-propanamide hemisuccinate A solution of Intermediate 3 (0.5 g) as the free base, in anhydrous freshly distilled tetrahydrofuran (25 ml) containing triethylamine (0.21 ml) was cooled to ca −15° and treated with acetic anhydride (0.143 ml). The solution was stirred at −15° for 0.5 h., allowed to reach room temperature over a period of 1.5 h., and then stirred at room temperature for 18 h. The mixture was evaporated to dryness and the residual gum (1.0 g) combined with a similarly prepared sample (0.2 g). Flash chromatography (A) presented the title compound free base as a foam (0.41 g), a solution of which (0.388 g) in hot ethyl acetate (5 ml) was treated with a hot solution of succinic acid (0.056 g) in absolute alcohol (2 ml). Evaporation to dryness gave the title compound as a foam (0.377 g) m.p. 80°–85° (dec).

N.m.r. δ includes 2.03 (3H, s, —COCH$_3$), 2.4–2.55 (8H, m, NMe$_2$ and —CH$_2$CH$_2$CO—, 2.6–3.0 (6H, m, —CH$_2$CH$_2$N— and —CH$_2$CH$_2$CO), 4.2 (2H, d, —CH$_2$N), 8.3 (1H, t, —CONHCH$_2$—) and 10.66 (1H, br, indole NH).

EXAMPLE 2

3-[2-(Dimethylamino)ethyl]-N-[[4-[(methylsulphonyl-)amino]phenyl]methyl]-1H-indole-5-propanamide hemisuccinate A solution of Intermediate 3 (0.38 g) as the free base in pyridine (10 ml), at −15°, was treated with methanesulphonyl chloride (0.087 ml) and the resulting solution stirred for 24 h at room temperature. After cooling to −15°, a further portion of methanesulphonyl chloride (0.01 ml) was added and stirring continued at room temperature for 18 h. The solution was evaporated to dryness, preabsorbed onto silica gel and purified by flash chromatography. (A and D). Evaporationn of the appropriate fractions produced the title compound free base as a glass (0.227 g), a solution of which (0.272 g) in hot absolute ethanol (2 ml)/ethyl acetate (2 ml) was treated with a hot solution of succinic acid (36.3 mg) in absolute ethanol (2 ml). The solvent was removed by evaporation and the residue triturated successively with ethyl acetate and ether to give the title compound as a powder (0.23 g) m.p. 78°–82°. N.m.r. δ includes 2.33 (6H, s, NMe$_2$), 2.48 (br t, CH$_2$CH$_2$CO—), 2.66 and 2.84 (2×2H, 2×½AA′BB′, —CHNMe$_2$ and —CH$_2$NMe$_2$), 2.90 (m, —COCH$_2$CH$_2$), 2.95 (s, MeSO$_2$—), 4.22 (2H, d, NHC$\underline{H}_2$), 8.3(1H, t, CH$_2$N$\underline{H}$CO—) and 10.8 (1H, br s, indole N$\underline{H}$).

EXAMPLE 3

N-[[4-(Aminosulphonyl)phenyl]methyl]-3-[2-(dimethylamino)ethyl]-1$\underline{H}$-indole-5-propanamide, oxalate A suspension of Intermediate 5 (0.52 g) in dry pyridine (15 ml) at −17° (cooling bath temperature) was treated with thionyl chloride (0.22 ml) and stirred for 40 min. The cooling bath (now −8°) was replenished and 4-(aminosulphonyl)benzylamine hydrochloride (0.4 g) was added portionwise at −14° (cooling bath temperature) to the reaction flask. The mixture was stirred and allowed to reach room temperature over a period of 6 h and then allowed to stand at room temperature for 3 days. The solvent was removed by evaporation and the residual material dissolved in methanol (2 ml) and chromatographed (8). Evaporation of the appropriate fractions produced a foam which was purified by HPLC to give the title compound free base as a foam (0.28 g) m.p. 80°–90°. The free base (0.278 g) in hot isopropanol (2 ml) was treated with a hot solution of oxalic acid (0.05841 g) in isopropanol (2 ml). A further quantity of isopropanol (4 ml) was added and the mixture heated to boiling point. The oxalate salt crystallised on cooling and was filtered off and washed with cold isopropanol (2 ml) to give the title compound as a solid (0.28 g) m.p. 125°–135°.

Analysis Found: C, 54.7; H, 6.0; N, 10.6. C$_{22}$H$_{28}$N$_4$O$_3$S.C$_2$H$_2$O$_4$0.1C$_3$H$_8$O.0.25H$_2$O requires C, 55.1; H, 6.0; N, 10.6%.

EXAMPLE 4

N-[4-[[(Methylamino)sulphonyl]methyl]phenyl]-3-[2-(dimethylamino)ethyl]-1-$\underline{H}$-indole-5-propanamide oxalate A suspension of Intermediate 5 (0.52 g) in anhydrous pyridine (5 ml) at −17° was treated with thionyl chloride (0.22 ml). The resulting solution was stirred for 3 h during which time the temperature reached 10°. The reaction mixture was again cooled to −17°, treated with 4-(aminosulphonyl)benzylamine hydrochloride (0.4256 g) and allowed to reach room temperature over a period of 2 h. Stirring was continued for a further 44 h. The solution was evaporated to dryness and the residue purified by flash chromatography (D and A). Evaporation of the appropriate fractions gave the free base as semi solid (0.395 g) a solution of which (0.39 g) in hot isopropanol (4 ml) was treated with a hot solution of oxalic acid (0.0823 g) in hot isopropanol (2 ml). The solvent was removed by rotary evaporation to give the oxalate salt as a solid (0.4 g) m.p. 75°–80°.

N.m.r. δ (D$_2$O) includes 2.74–2.80 (8H, s+m, NMe$_2$ and —CH$_2$C$\underline{H}_2$CO), 3.04–3.36 (6H, m, ;C$\underline{H}_2$CH$_2$NMe$_2$, —CH$_2$C$\underline{H}_2$NMe$_2$ and —C$\underline{H}_2$CH$_2$CO—) and 4.42 (2H, s, —C$\underline{H}_2$SO$_2$—).

EXAMPLE 5

3-[2-(Dimethylamino)ethyl]-N-[[3-[(methylsulphonyl)amino]phenyl]methyl]-1$\underline{H}$-indole-5-propanamide oxalate A suspension of Intermediate 5 (0.3 g) in anhydrous dimethylformamide (15 ml) was treated with triethylamine (0.33 ml) diphenylphosphorylazide (0.51 ml) and 3-(methylsulphonylamino)benzylamine (0.231 g). The resultant suspension was stirred at room temperature and a solution was formed after 6 h. Stirring at room temperature was continued for 48 h. The solvent was removed by evaporation and the resulting oil purified by flash chromatography (F, G, A, D). Evaporation of the appropriate fractions gave the title compound free base as a foam (0.4185 g). A solution of the free base (0.4013 g) in methanol (1 ml) was treated with a solution of oxalic acid (0.0843 g) in methanol (1 ml) and the solution evaporated to dryness to give the title compound as a foam (0.42 g) m.p. 70°–75°.

N.m.r. δ includes 2.5 (2H, m, —COCH$_2$CH$_2$—), 2.85 (6H, s, —NMe$_2$), 2.9–3.0 (2H, ½AA'BB', —CH$_2$CH$_2$CO—), 3.0–3.35 (4H, AA'BB', —C$\underline{H}_2$CH$_2$NMe$_2$ and —CH$_2$C$\underline{H}_2$NMe$_2$), 8.42 (1H, brt, —C$\underline{H}_2$NHCO—), 9.7 (1H, brs, MeSO$_2$N$\underline{H}$) and 10.8 (1H, brs, indole N$\underline{H}$).

EXAMPLE 6

N-[[4-(2-Amino-2-oxoethyl)phenyl]methyl]-3-[2-(dimethylamino)ethyl]-1$\underline{H}$-indole-5-propanamide, (2R,3R)-L-(+)-tartrate A solution of Intermediate 7 as the free base (0.6 g) in ethanol (15 ml) was treated with 0.88 ammonium hydroxide (25 ml) and stirred at room temperature for 24 h. A further quantity of ammonia (10 ml) was added and stirring continued for another 20 h. The solvent was removed by rotary evaporation and the residual foam (0.9 g) chromatographed (B) to yield a semi-solid (0.53 g). Further chromatography (B) produced the free base as a gum (0.225 g). A solution of the free base (0.197 g) in absolute ethanol (2 ml) was treated with a solution of (+)-tartaric acid (0.07273 g) in absolute alcohol (2 ml). The alcohol was decanted from the precipitated salt which was triturated with anhydrous ether to give the title compound as a powder (0.11 g) m.p. 68°–71°.

N.m.r. δ includes 2.26 (6H, s, NMe$_2$), 2.50 (m, —C$\underline{H}_2$NMe$_2$ and —CH$_2$CH$_2$CO—), 2.82 (2H, ½AA'BB', —CH$_2$C$\underline{H}_2$NMe$_2$), 2.95 (2H, t—C$\underline{H}_2$CH$_2$CO—), 3.38 (2H, s, —C$\underline{H}_2$CONH$_2$), 4.28 (2H, d, —C$\underline{H}_2$NH—), 6.91 and 7.5 (2×1H, 2×brs, —NH$_2$), 8.35 (1H, brt, —CH$_2$N$\underline{H}$CO—) and 10.8 (1H, brs, indole N$\underline{H}$).

EXAMPLE 7

N-[[4-(2-Amino-2-oxoethyl)phenyl]methyl]-3-[2-(ethylamino)ethyl]-1$\underline{H}$-indole-5-propanamide oxalate A solution of Intermediate 10 (0.3 g) in ethanolic ethylamine solution (80 ml of 33% w/w ethylamine in ethanol) was hydrogenated in the presence of 10% palladium oxide on carbon [0.3 g of a 50% paste with water, pre-reduced in ethanol (20 ml)]. The hydrogenation was continued at room temperature and atmospheric pressure for 69 h. The catalyst and solvent were removed by filtration and rotary evaporation to give a glass (0.31 g) which was purified by flash chromatography (B). Evaporation of the appropriate fractions gave the title compound free base as a gum (0.197 g) a solution of which (0.191 g) in hot methanol (3 ml) was treated with oxalic acid (0.0423 g) in hot methanol (2 ml). The solvent was removed leaving the oxalate as a gum. Prolonged stirring with anhydrous ether gave the title compound as a cream powder (0.171 g) m.p. 50° (dec.)

N.m.r. δ includes 1.2 (t, —NHCH$_2$C$\underline{H}_3$), 2.5 (m, —NHC$\underline{H}_3$), 2.9–3.2 (8H, m, —NHC$\underline{H}_2$CH$_3$, —CH$_2$CH$_2$N—, —C$\underline{H}_2$CH$_2$N and —COC$\underline{H}_2$CH$_2$), 3.35 (s, H$_2$NCOC$\underline{H}_2$—), 4.24 (2H, d, —C$\underline{H}_2$NHCO—), 6.88 and 7.48 (2×1$\underline{H}$, 2×brs, —N$\underline{H}_2$) and 10.8 (1H, brs, indole N$\underline{H}$).

The following examples illustrate pharmaceutical formulations according to the invention, containing 3-[2-(dimethylamino)ethyl]-N-[[4-[(methylsulphonyl)amino]phenyl]methyl]-1H-indole-5-propanamide hemisuccinate as the active ingredient. Other compounds of the invention may be formulated in a very similar manner.

TABLETS FOR ORAL ADMINISTRATION

| DIRECT COMPRESSION | mg/tablet |
| --- | --- |
| Active ingredient | 2.4 |
| Calcium hydrogen phosphate B.P.* | 95.10 |
| Croscarmellose sodium USP | 2.00 |
| Magnesium stearate, B.P. | 0.50 |
| Compression weight | 100 mg |

*of a grade suitable for direct compression

The active ingredient is sieved before use. The calcium hydrogen phosphate, croscarmellose sodium and active ingredient are weighed into a clean polythene bag. The powders are mixed by vigorous shaking then the magnesium stearate is weighed and added to the mix which is blended further. The mix is then compressed using a Manesty F3 tablet machine fitted with 5.5 mm flat bevelled edge punches, into tablets with target compression weight of 100 mg.

Tablets may also be prepared by other conventional methods such as wet granulation.

Tablets of other strengths may be prepared by altering the ratio of active ingredient to lactose or the compression weight and using punches to suit.

The tablets may be film coated with suitable film forming materials, such as hydroxypropyl methylcellulose, using standard techniques. Alternatively the tablets may be sugar coated.

CAPSULES

| | mg/capsule |
| --- | --- |
| Active ingredient | 2.4 |
| *Starch 1500 | 196.6 |
| Magnesium Stearate BP | 1.00 |
| Fill Weight | 200.00 |

*A form of directly compressible starch.

The active ingredient is sieved and blended with the excipients. The mix is filled into size No. 2 hard gelatin capsules using suitable machinery. Other doses may be prepared by altering the fill weight and if necessary changing the capsule size to suit.

SYRUP

| | mg/5 ml dose |
| --- | --- |
| Active ingredient | 2.4 |
| Buffer | |
| Flavour | |
| Colour | as required |
| Preservative | |
| Thickening agent | |
| Sweetening agent | |
| Purified Water to | 5.00 ml |

The active ingredient, buffer, flavour, colour, preservative, thickening agent and sweetening agent are dissolved in some water, the solution is adjusted to volume and mixed. The syrup produced is clarified by filtration.

SUPPOSITORY FOR RECTAL ADMINISTRATION

| | |
| --- | --- |
| Active ingredient | 2.4 mg |
| * Witepsol H15 to | 1.0 g |

* A proprietary grade of Adeps Solidus Ph. Eur.

A suspension of the active ingredient in molten Witepsol is prepared and filled, using suitable machinery, into 1 g size suppository moulds.

INJECTION FOR INTRAVENOUS ADMINISTRATION

| | mg/ml |
| --- | --- |
| Active ingredient | 0.6 mg |
| Sodium Chloride BP | as required |
| Water for Injection BP to | 1.0 ml |

Sodium chloride may be added to adjust the tonicity of the solution and the pH may be adjusted, using acid or alkali, to that of optimum stability and/or to facilitate solution of the active ingredient. Alternatively suitable buffer salts may be used.

The solution is prepared, clarified and filled into appropriate size ampoules sealed by fusion of the glass. The injection is sterilised by heating in an autoclave using one of the acceptable cycles. Alternatively the solution may be sterilised by filtration and filled into sterile ampoules under aseptic conditions. The solution may be packed under an inert atmosphere of nitrogen or other suitable gas.

We claim:

1. Compounds of the formula (I):

$$R_1\text{-Ar-}(CH_2)_m\text{-NCO}(CH_2)_n\text{-[indole]-}(CH_2)_2NR_3R_4$$
(with $R_2$ on the nitrogen of NCO)

wherein $R_1$ represents a group $R_5R_6NCOCH_2-$, a group $R_5CONH(CH_2)_p-$, a group $R_5R_6NSO_2(CH_2)_p-$ or a group $R_7SO_2NH(CH_2)_p-$, (where $R_5$ and $R_6$, which may be the same or different, each represents a hydrogen atom or a $C_{1-3}$ alkyl group, $R_7$ represents a $C_{1-3}$ alkyl group and p is zero or one), $R_2$ represents a hydrogen atom or a $C_{1-3}$ alkyl group;

$R_3$ and $R_4$ which may be the same or different each represents a hydrogen atom, a $C_{1-3}$ alkyl group, or a 2-propenyl group;

m is zero or an integer from 1 to 4; and n is an integer from 2 to 5;

and physiologically acceptable salts thereof.

2. Compounds according to claim 1, wherein in the formula (I), $R^1$ represents a $H_2NCOCH_2$ or $CH_3SO_2NH$ group.

3. Compounds according to claim 1, wherein, in the formula (I), m is 1.

4. Compounds according to claim 1, wherein, in the formula (I), n is 2.

5. Compounds according to claim 1, wherein, in the formula (I), $R^2$ represents a hydrogen atom.

6. Compounds according to claim 1, wherein, in the formula (I), $R^3$ and $R^4$, each represents a methyl group.

7. Compounds selected from 3-[2-(Dimethylamino)ethyl]-N-[[4-methylsulphonyl)amino]phenyl]methyl]-1H-indole-5-propanamide; 3-[2-(Dimethylamino)ethyl]-N-[[4-(2-amino-2-oxoethyl)phenyl]methyl]-1H-indole-5-propanamide; and physiologically acceptable salts thereof.

8. A pharmaceutical composition which comprises at least one compound of formula (I) as defined in claim 1, or a physiologically acceptable salt thereof together with one or more pharmaceutically acceptable carriers or excipients.

9. A compound according to claim 5, wherein, in the formula (I), $R^3$ and $R^4$, each represents a methyl group.

10. A method of treating a patient susceptible to or suffering from migraine which comprises administering to the patient an effective amount of a compound of formula (I) as defined in claim 1 or a physiologically acceptable salt or thereof.

11. A method of treating a patient susceptible to or suffering from migraine which comprises administering to the patient a pharmaceutical composition as claimed in claim 8.

12. A compound according to claim 4, wherein, in the formula (I), $R^3$ and $R^4$, each represents a methyl group.

13. A compound according to claim 2 wherein, in the formula (I), m is 1.

14. A compound according to claim 2 wherein, in the formula (I), wherein n is 2.

15. A compound according to claim 3 wherein, in the formula (I), n is 2.

16. A compound according to claim 2, wherein, in the formula (I) $R^2$ represents a hydrogen atom.

17. A compound according to claim 3, wherein, in the formula (I) $R^2$ represents a hydrogen atom.

18. A compound according to claim 4, wherein, in the formula (I) $R^2$ represents a hydrogen atom.

19. A compound according to claim 2, wherein, in the formula (I), $R^3$ and $R^4$, each represents a methyl group.

20. A compound according to claim 3, wherein, in the formula (I), $R^3$ and $R^4$, each represents a methyl group.

* * * * *